United States Patent
Mikami et al.

(10) Patent No.: US 7,459,570 B2
(45) Date of Patent: Dec. 2, 2008

(54) HIGH-PURITY BIPHENYLTETRACARBOXYLIC DIANHYDRIDE AND PROCESS FOR PRODUCING THE SAME

(75) Inventors: Hiroshi Mikami, Kitakyushu (JP); Takeshi Sano, Kitakyushu (JP); Makoto Nitta, Kitakyushu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 496 days.

(21) Appl. No.: 10/753,881

(22) Filed: Jan. 9, 2004

(65) Prior Publication Data

US 2004/0199010 A1  Oct. 7, 2004

(51) Int. Cl.
*C07D 307/00* (2006.01)
*C07D 493/04* (2006.01)

(52) U.S. Cl. ........................ 549/236; 549/239

(58) Field of Classification Search .................. 562/867
See application file for complete search history.

(56) References Cited

U.S. PATENT DOCUMENTS 4,958,002 A * 9/1990 Imatani et al. .............. 528/353
5,047,560 A * 9/1991 Shoji et al. .................. 549/241

FOREIGN PATENT DOCUMENTS

| JP | 61-249977 | 11/1986 |
| JP | 64-050876 | 2/1989 |
| JP | 08-134056 | 5/1996 |
| JP | 08-134057 | 5/1996 |
| JP | 2003-335768 | 11/2003 |
| WO | WO0100710 | * 1/2001 |

OTHER PUBLICATIONS

Richard J. Lewis, Sr., Hawley's Condensed Chemical Dictionary, twelfth edition, 1993, pp. 300, 301, 960 and 961.*

* cited by examiner

*Primary Examiner*—Rosalynd Keys
(74) *Attorney, Agent, or Firm*—Nixon & Vanderhye P.C.

(57) ABSTRACT

There is provided biphenyltetracarboxylic dianhydride containing biphenyltetracarboxylic monoanhydride in an amount of not more than 0.4%. By using the biphenyltetracarboxylic dianhydride as a raw material, it is possible to produce polyimide or polyamic acid having an increased molecular weight.

2 Claims, No Drawings

HIGH-PURITY BIPHENYLTETRACARBOXYLIC DIANHYDRIDE AND PROCESS FOR PRODUCING THE SAME

BACKGROUND OF THE INVENTION

The present invention relates to biphenyltetracarboxylic dianhydride and a process for producing the biphenyltetracarboxylic dianhydride, and more particularly, to high-purity biphenyltetracarboxylic dianhydride having much less contents of impurities and water which inhibit the production of high-molecular polyimide or polyamic acid from the biphenyltetracarboxylic dianhydride, and a process for stably producing the biphenyltetracarboxylic dianhydride.

Biphenyltetracarboxylic dianhydride (hereinafter occasionally referred to merely as "BPDA") is a useful compound as a raw material for production of aromatic polyimides that have been noticed as heat-resistant resins. The aromatic polyimides can be produced from the raw BPDA by a method of polymerizing BPDA with aromatic diamines, a method of subjecting a polyamic acid obtained by polymerizing BPDA with an aromatic diamine at a low temperature near an ordinary temperature to ring-closing imidization reaction, or the like.

The BPDA has been generally produced by subjecting biphenyltetracarboxylic acid (hereinafter referred to merely as "BTC") to dehydration ring-closing reaction. The BTC can be produced, for example, by the following methods (i) and (ii).

(i) Method of subjecting tetramethyl biphenyltetracarboxylate obtained by dehydrogenation dimerization reaction of dimethyl o-phthalate to hydrolysis in an aqueous medium in the presence of an acid catalyst.

(ii) Method of subjecting 4-halophthalic acid obtained by halogenating phthalic anhydride to dehalogenation dimerization reaction in an aqueous medium in the presence of an alkali, a reducing agent and a Pb catalyst to obtain an aqueous solution of a tetraalkaline metal salt of biphenyltetracarboxylic acid, and then neutralizing the tetraalkaline metal salt of biphenyltetracarboxylic acid with a mineral acid.

When BPDA containing impurities such as biphenyltricarboxylic anhydride is used to produce the above polymers, the increase in polymerization degree (viscosity) thereof is inhibited, thereby failing to produce high-molecular polyimide or polyamic acid. Accordingly, there have been proposed various methods of preventing discoloration, inclusion of fine insoluble particles as well as a trace amount of metals, or production of other impurities when the BPDA is produced by subjecting the BTC to dehydration ring-closing reaction.

For example, there has been proposed a method of heating BTC in a solid state to a temperature of 150 to 230° C. to subject the BTC to dehydration ring-closing reaction for obtaining BPDA, vaporizing the thus obtained BPDA by heating to a temperature of 250 to 400° C. under reduced pressure, and then cooling the vapor of the BPDA to recover the BPDA in the form of purified crystals (for example, refer to Japanese Patent Publication (KOKOKU) No. 4-37078).

However, the above method only may fail to prevent biphenyltricarboxylic anhydride (hereinafter referred to merely as "tri-compound") as impurity to be mixed in the aimed product, thereby inhibiting the production of high-molecular polyimide or polyamic acid. The tri-compound tends to be mainly produced at the dehydration ring-closing reaction stage in which the BTC is heated to a temperature of 150 to 230° C. and at the temperature rise stage in which the BPDA is heated to a temperature of 250 to 400° C.

For the purpose of inhibiting production of the tri-compound, it has been attempted to remove water such as adhering water and crystal water from the BPDA. For example, there has been proposed a method of heating BPDA up to a temperature capable of removing water therefrom at a temperature rise rate of not more than 50° C./hr, and then successively heating the BPDA at a temperature of 250 to 300° C. for at least 3 hours to completely remove water from the BPDA (for example, Japanese Patent Application Laid-Open (KOKAI) No. 1-104063).

Alternatively, there has been proposed a method for producing BPDA by heat-treating BTC in which the BTC is contacted with an inert gas at a temperature of 250 to 300° C. for 8 to 40 hours to produce the BPDA while removing a tri-compound thereof as a by-product from a reaction mixture (for example, refer to Japanese Patent Publication (KOKOKU) No. 4-76991).

However, the above conventional methods have such a problem that even if the production of the tri-compound is prevented, the resultant aromatic polyimide may still fail to show a sufficiently enhanced viscosity (i.e., not improved in molecular weight). The reason therefor has been considered to be that BPDA is hydrolyzed by water absorbed therein to ring-open one of acid anhydride groups of BPDA, thereby producing biphenyltetracarboxylic monoanhydride (hereinafter referred to merely as "half compound") which tends to exist as impurity in the resultant polymer. That is, the half compound having an anhydride group contributing to the polymerization and a carboxyl group not contributing thereto, tends to produce a polymerization-inhibiting terminal group like the tri-compound when producing the aromatic polyimide by polymerization of BPDA. However, there have been proposed no effective methods for preventing the production of the half compound.

Also, although it is considered that water absorbed in BPDA is present in the form of free water, crystal water or water for ring-opening the cyclic anhydride group of BPDA, the configuration of water contained in BPDA as well as the influence of the water on molecular weight of the resultant aromatic polyimide, etc, have not been clearly recognized. Therefore, at present, any effective water-removing methods for preventing the production of the half compound are still unknown.

Upon the production of the aromatic polyimide, BPDA is generally pulverized into fine particles before being subjected to the reaction. However, since BPDA has a moisture-absorbing property, the pulverization of BPDA tends to cause problems such as increase in water absorption due to increased surface area thereof. More specifically, when a reactor of a chemical industrial scale is used, the fine BPDA particles are blown up in a gas-phase portion of the reactor and frequently contacted with outside air therein, so that water present in the gas-phase portion tends to be absorbed in the fine BPDA particles, resulting in risk of production of the above half compound as impurity.

Therefore, in order to prevent undesirable water absorption in BPDA and produce a high-quality aromatic polyimide, an inside of the reactor used for producing the aromatic polyimide must be kept under excessively dried condition since drying conditions of the inside of the reactor are not clearly known, thereby causing problems such as increased industrial costs.

SUMMARY OF THE INVENTION

An object of the present invention is to provide BPDA that is suitable for production high-molecular aromatic polyimide. More specifically, an object of the present invention is to provide BPDA having a less content of a half compound as a decomposed product of BPDA, which inhibits the production of the high-molecular aromatic polyimide, by preventing the absorption of water into BPDA upon production of BPDA as well as the decomposition of produced BPDA due to water absorbed therein.

As a result of the present inventors' earnest studies for solving the above problems by inhibiting water from being absorbed in BPDA upon pulverization thereof and further preventing water absorbed in BPDA from being consumed for ring-opening of anhydride groups in BPDA, it has been found that when BPDA is pulverized not under an atmosphere whose water content is simply reduced, but under an inert gas atmosphere having a specific water content of not more than a predetermined value and a specific temperature of not more than a predetermined temperature, preferably under a flow of such an inert gas, it becomes possible to not only reduce an amount of water absorbed therein, but also prevent water absorbed in BPDA from being consumed for ring-opening of the anhydride groups in BPDA, more specifically, to minimize a content of the half compound, etc., as impurities which inhibit the production of high-molecular aromatic polyimide. The present invention has been attained on the basis of the above finding.

In addition, it has been found that when the water content in BPDA is measured by heating the BPDA up to an arrival temperature of 248° C. using a vaporization-type water content meter, there is not necessarily present a specific relation between the thus measured water content in BPDA and the viscosity of aromatic polyimide produced from BPDA.

On the other hand, it has been found that in measurement of the water content in BPDA, when the amount of water vaporized from BPDA is measured, the amounts of free water and crystal water contained in BPDA can be measured by heating the BPDA up to an arrival temperature of 210° C., and the amount of water generated upon converting ring-opened products of BPDA into an anhydride thereof can be measured by heating the BPDA up to an arrival temperature of 248° C.

Moreover, on the basis of the above finding, it has been found that the viscosity of the obtained polymer varies depending upon the change in ratio between configurations of water contained in BPDA, and the viscosity of the polymer is most significantly influenced by such a configuration of water contained in BPDA in which the amount of water consumed for ring-opening of the anhydride groups in BPDA is larger.

Namely, it has been found that not only when the water content in BPDA is small as measured under a single condition, but also when the difference between water contents as respectively measured under a plurality of specific conditions is not more than a predetermined value, the BPDA is suitably used as an excellent raw material for production of the aromatic polyimide. The present invention has been attained on the basis of this finding.

In one aspect of the present invention, there is provided biphenyltetracarboxylic dianhydride containing biphenyltetracarboxylic monoanhydride in a total amount of not more than 0.4%.

More preferably, in a temperature rise process including heating the biphenyltetracarboxylic dianhydride from 20° C. to 248° C. and then maintaining a temperature of the biphenyltetracarboxylic dianhydride at 248° C. for 30 minutes after reaching 248° C., the total amount of water vaporized from the biphenyltetracarboxylic dianhydride during the whole period of the temperature rise process is not more than 500 ppm, and the amount of water vaporized from the biphenyltetracarboxylic dianhydride during the period of the temperature rise process subsequent to reaching 210° C. is not more than 200 ppm.

In another aspect of the present invention, there is provided a process for producing the biphenyltetracarboxylic dianhydride, which comprises the step of pulverizing the biphenyltetracarboxylic dianhydride under an inert gas atmosphere having a water content of not more than 200 ppm and a temperature of not more than 30° C.

DETAILED DESCRIPTION OF THE INVENTION

The present invention is described in detail below.

(1) Biphenyltetracarboxylic dianhydride:

The biphenyltetracarboxylic dianhydride of the present invention contains biphenyltetracarboxylic monoanhydride (half compound) in a total amount of not more than 0.4 wt %. The content of the half compound is preferably as low as possible, but is usually not less than 0.1 wt %. In addition, when the biphenyltetracarboxylic dianhydride is subjected to such a temperature rise process including heating the biphenyltetracarboxylic dianhydride from 20° C. to 248° C. and then maintaining a temperature of the biphenyltetracarboxylic dianhydride at 248° C. for 30 minutes after reaching 248° C., the total amount of water vaporized from the biphenyltetracarboxylic dianhydride during the whole period of the temperature rise process is preferably not more than 500 ppm, and the amount of water vaporized from the biphenyltetracarboxylic dianhydride during the period of the temperature rise process subsequent to reaching 210° C. is preferably not more than 200 ppm.

The amount of the half compound contained in the BPDA can be measured by a high-performance liquid chromatography.

The total amount of water vaporized from the biphenyltetracarboxylic dianhydride during the whole period of the temperature rise process including heating the biphenyltetracarboxylic dianhydride from 20° C. to 248° C. and then maintaining a temperature of the biphenyltetracarboxylic dianhydride at 248° C. for 30 minutes after reaching 248° C., is usually not more than 500 ppm, preferably not more than 300 ppm, more preferably not more than 150 ppm. When the total amount of water vaporized from the BPDA in the above temperature rise process is too large, it indicates that the BPDA contains a large amount of ring-opened products thereof. As a result, it may be difficult to polymerize the BPDA with diamines, thereby occasionally failing to sufficiently enhance a viscosity of the resultant polyimide. Also, although the total amount of water vaporized from the BPDA in the above temperature rise process is preferably as low as possible as long as the amount is not more than 500 ppm, much reduction in the total amount of water vaporized tends to require large costs and, therefore, tends to be undesirable from industrial viewpoints. For this reason, in general, the total amount of water vaporized from the BPDA in the above temperature rise process is suitably about 200 ppm.

Further, in the above temperature rise process including heating the BPDA from 20° C. to 248° C. and then maintaining the temperature of the BPDA at 248° C. for 30 minutes after reaching 248° C., the amount of water vaporized from the BPDA during the period of the temperature rise process subsequent to reaching 210° C. is usually not more than 200 ppm, preferably not more than 100 ppm, more preferably not more than 50 ppm. When the above amount of water vaporized during the period of the temperature rise process subsequent to reaching 210° C. is too large, the amount of the half compound contained in the BPDA increases, thereby causing such a problem that the viscosity of the resultant polyimide is not sufficiently enhanced. Although the amount of water vaporized from the BPDA during the period of the temperature rise process subsequent to reaching 210° C. is preferably as low as possible as long as the amount thereof is not more than 200 ppm, much reduction in the amount of water vaporized tends to require large costs and, therefore, tends to be disadvantageous from industrial viewpoints. For this reason, in general, the amount of water vaporized from the BPDA during the period of the temperature rise process subsequent to reaching 210° C. is more preferably about 100 ppm.

In the present invention, upon measuring the amount of water vaporized by heating the BPDA, the amount of water vaporized from the BPDA is measured from 20° C. In this case, the temperature of BPDA at which the heating thereof is initiated is optional, and the measurement may be initiated using BPDA having a temperature of less than 20° C. The temperature of BPDA used herein usually means the temperature of BPDA itself, but upon measuring the concentration of water vaporized from BPDA, the temperature represents an inside temperature of a measuring device used. Meanwhile, upon initiation of measuring the amount of water vaporized from the temperature of BPDA represents a temperature of an ambient atmosphere around the BPDA.

The temperature rise rate used upon the measurement is also optional, and may be appropriately selected as long as the measurement can be accurately performed. The temperature rise rate is usually 5 to 20° C./min, preferably 10 to 15° C./min. When the temperature rise rate is too high, it may be difficult to cause the temperature of BPDA to follow the temperature rise atmosphere. On the contrary, when the temperature rise rate is too low, the difference between the actual temperature of BPDA and the surrounding temperature rise atmosphere tends to become too large, thereby failing to accurately measure the amount of water vaporized.

Meanwhile, the reason why the viscosity of the obtained polymer varies depending upon the configuration of water absorbed in BPDA even if the amount of water absorbed is the same, is not clearly known. However, it is considered that the reason why the viscosity of the obtained polymer is not considerably lowered even if the amount of free water or crystal water is more or less increased, is that the velocity of polymerization between BPDA and amine is higher than the velocity of ring-opening reaction of anhydride groups in BPDA.

BPDA according to the present invention may be produced by any optional methods. Among them, the following production method is preferable to reduce amounts of impurities or water contained in the obtained BPDA.

(2) Process for Producing Biphenyltetracarboxylic Dianhydride:

The process for producing the biphenyltetracarboxylic dianhydride according to the present invention comprises the step of pulverizing the biphenyltetracarboxylic dianhydride in an inert gas atmosphere having a water content of not more than 200 ppm and a temperature of not more than 30° C.

BPDA to be pulverized according to the above process may be produced by any optional known methods. Among them, there may be preferably used a so-called sublimation method as described in the above Japanese Patent Publication (KOKOKU) No. 4-37078, which method includes the steps of heating BTC in a solid state to subject the BTC to dehydration ring-closing reaction for obtaining BPDA, heating and vaporizing the resultant BPDA under reduced pressure, and then cooling the vapor of BPDA to recover BPDA as purified crystals, because the BPDA produced by this method can be reduced in content of impurities, etc.

The amount of water contained in the thus obtained BPDA is preferably as small as possible, and is usually 100 to 500 ppm. The particle size of BPDA before the pulverization may also be optional. For example, BPDA obtained by the above sublimation method may have a particle size of usually 1 to 1,000 μm, preferably 1 to 700 μm.

The process for producing the BPDA according to the present invention includes the step of pulverizing the thus obtained BPDA in an inert gas atmosphere having a water content of not more than 200 ppm and a temperature of not more than 30° C.

In particular, in order to conduct the pulverization under the above inert gas atmosphere, the BPDA is preferably pulverized under a flow of such an inert gas. The velocity and feed amount of the inert gas flow may also be optional. For example, when the volume of a region where the pulverization of BPDA is performed is 14 liters, the inert gas may be supplied from an inlet port having a diameter of 15 mm under a pressure of 6,000 Pa, and discharged through an outlet port having a diameter of 15 mm. Meanwhile, in general, the inlet and outlet ports for the inert gas may be spaced apart from each other at as large a distance as possible.

The kind of inert gas used in the process of the present invention is optional, and any inert gases may be used as long as they are inert to BPDA, i.e., are substantially free from chemical reactions with BPDA. Specific examples of the inert gas may include nitrogen, rare gases such as helium and argon, or the like. The inert gas is required to have a water content of not more than 200 ppm, preferably not more than 150 ppm, more preferably not more than 100 ppm and still more preferably not more than 50 ppm.

In addition, the inert gas is required to have a temperature of not more than 30° C. When the temperature of the inert gas is too high, for example, as high as not less than 50° C., the amount of water used for ring-opening reaction of the anhydride groups in BPDA tends to be increased even though the water content of the inert gas is low. This reason is considered to be that the increased temperature of the inert gas tends to promote the ring-opening reaction of the anhydride groups during the pulverization process.

Although the temperature of the inert gas is suitably controlled to not more than 30° C., if the temperature of the inert gas is too low, water vapor tends to be condensed. Therefore, the temperature of the inert gas is in the range of usually 0 to 30° C., preferably 15 to 25° C.

The particle size of the BPDA after being pulverized is usually 1 to 500 μm, preferably 1 to 200 μm. In addition, from the standpoint of minimizing the amount of water absorbed in the BPDA, the residence time of the BPDA within a pulverizer is usually 5 seconds to 5 minutes, preferably 5 seconds to one minute.

When the biphenyltetracarboxylic dianhydride of the present invention is used, it is possible to increase the molecular weight of the obtained polyimide or polyamic acid, resulting in production of excellent polymers. In addition, the process for producing biphenyltetracarboxylic dianhydride according to the present invention enables a simple production of the biphenyltetracarboxylic dianhydride.

EXAMPLES

The present invention is described in more detail below by Example, but this Example is not intended to limit the scope of the present invention. Meanwhile, the polymerization test for BPDA described in the following Example and Comparative Examples was performed by the following method.

<Method for Measuring Water Content in BPDA>

1 g of a sample to be measured was weighed, placed in a water vaporization apparatus "VA-100" and a trace water content measuring device "CA-100 Model" both manufactured by Mitsubishi Kagaku Co., Ltd., and then heated at a temperature rise rate of 10° C./min up to 210° C. at which heating was automatically terminated and then an amount of water vaporized from the sample was measured. Further, the temperature was raised to 248° C. at which heating was automatically terminated, and the sample was maintained at 248° C. for 30 minutes. The amount of water vaporized from the sample corresponds to that of ring-opened anhydride groups in BPDA.

<Analysis of Half Compound in BPDA>

The half compound was analyzed by a high-performance liquid chromatography (hereinafter referred to merely as "LC"). Upon the measurement of the half compound, the BPDA sample was pretreated to convert the BPDA and the half compound into respective derivatives, thereby separating respective peaks on LC curve from each other for quantity determination thereof.

Example 1

<Purification of BPDA>

100 parts by weight of BTC was charged into a vertical cylindrical reactor equipped with a stirrer, a jacket, a condenser, a thermometer and an inert gas feed port. The content of the reactor was heated to 215° C. under ordinary pressure while stirring, and a nitrogen gas was passed therethrough at a velocity of 2 m$^3$/hr. While removing water produced from the reaction system, the dehydration ring-closing reaction was continued at the same temperature for 10 hours, thereby obtaining crude BPDA. Successively, the thus obtained crude BPDA was heated to 300° C., and maintained at the same temperature for 5 hours to obtain a melt thereof.

The molten crude BPDA was transferred into a jacketed vertical cylindrical evaporator, and evaporated (vaporized) therein at 305° C. under a pressure of 230 Pa. The thus evaporated BPDA was fed through a gas conduit directly connected to a gas phase of the evaporator, and discharged from a tip end of the gas conduit onto the surface of a drum-type rotary cooler to contact therewith, thereby cooling and crystallizing the BPDA thereon. The BPDA crystals adhered onto the surface of the drum were continuously removed therefrom using a scraper, thereby recovering BPDA in the form of flakes.

<Pulverization of BPDA>

The resultant flakes of BPDA were pulverized using a pulverizer while flowing a nitrogen gas having a water content of 110 ppm and a temperature of 30° C. through a gas phase portion of the pulverizer. The pulverization time was 10 seconds. As a result of the measurement after the pulverization, it was confirmed that the obtained BPDA contained a half compound thereof in an amount of 0.2 wt %. Also, as a result of the measurement of water content in BPDA using the above vaporization-type water content meter, it was confirmed that the water concentration measured by heating the BPDA up to 248° C. was 500 ppm, and the water concentration measured by heating the BPDA up to 210° C. was 300 ppm.

<Polymerization of BPDA>

A 300-ml flask equipped with a stirrer and a nitrogen flow tube was charged with 11.76 g of BPDA obtained by the above method, 8 g of diaminodiphenyl ether and 177.84 g of N-methyl-2-pyrrolidone. The contents of the flask were stirred at 30° C. for 5.5 hours under a nitrogen flow to produce aromatic polyamic acid. N-methyl-2-pyrrolidone was added to the obtained reaction solution to prepare a solution having an aromatic polyamic acid concentration of 0.5 g/100 ml-solvent. The viscosity of the thus obtained solution was measured using an Ubbellohde viscometer at 30° C. The logarithmic viscosity was calculated from the thus measured viscosity according to the following formula:

Logarithmic Viscosity=ln (solution viscosity/solvent viscosity)/solution concentration As a result, the logarithmic viscosity was 3.6.

Comparative Example 1

The same procedure as defined in Example 1 was conducted except that upon pulverization of the BPDA flakes, the water content in the nitrogen gas flowing through the gas phase portion of the pulverizer was 1,000 ppm. As a result, it was confirmed that the amount of the half compound contained in the BPDA after being pulverized was 0.35 wt %, the water concentration measured by heating the BPDA up to 248° C. was 1,000 ppm, and the water concentration measured by heating the BPDA up to 210° C. was 800 ppm. The thus obtained BPDA was polymerized by the same method as defined in Example 1. As a result, it was confirmed that the logarithmic viscosity of the obtained aromatic polyamic acid was 2.9 and, therefore, the viscosity was lowered as compared to that of Example 1.

Comparative Example 2

The same procedure as defined in Example 1 was conducted except that upon pulverization of the BPDA flakes, the temperature of the nitrogen gas flowing through the gas phase portion of the pulverizer was 50° C. As a result, it was confirmed that the amount of the half compound contained in the BPDA after being pulverized was 0.6 wt %, the water concentration measured by heating the BPDA up to 248° C. was 500 ppm, and the water concentration measured by heating the BPDA up to 210° C. was 100 ppm. The thus obtained BPDA was polymerized by the same method as defined in Example 1. As a result, it was confirmed that the logarithmic viscosity of the obtained aromatic polyamic acid was 2.6 and, therefore, the viscosity was considerably deteriorated as compared to those of Example 1 and Comparative Example 1.

What is claimed is:

1. A process for producing purified biphenyltetracarboxylic dianhydride containing biphenyltetracarboxylic monoanhydride in an amount of not more than 0.4% comprising pulverizing the biphenyltetracarboxylic dianhydride under an inert gas atmosphere having a water content of not more than 200 ppm and a temperature of not more than 30° C.

2. A process for producing purified biphenyltetracarboxylic dianhydride containing biphenyltetracarboxylic monoanhydride in an amount of not more than 0.4% wherein in a temperature rise process including heating said biphenyltetracarboxylic dianhydride from 20° C. to 248° C. and then maintaining a temperature of the biphenyltetracarboxylic dianhydride at 248° C. for 30 minutes after reaching 248° C., a total amount of water vaporized from the biphenyltetracarboxylic dianhydride during a whole period of the temperature rise process is not more than 500 ppm, and an amount of water vaporized from the biphenyltetracarboxylic dianhydride during a period of the temperature rise process subsequent to a time at which the temperature of the biphenyltetracarboxylic dianhydride reaches 210° C. is not more than 200 ppm;

said process comprising pulverizing the biphenyltetracarboxylic dianhydride under an inert gas atmosphere having a water content of not more than 200 ppm and a temperature of not more than 30° C.

* * * * *